US012734277B2

(12) United States Patent
Fiorini et al.

(10) Patent No.: US 12,734,277 B2
(45) Date of Patent: Sep. 15, 2026

(54) CONTROLLED-VISCOSITY POLYMERIC HYDROGEL AND METHOD FOR MAKING IT

(71) Applicant: STERIFY S.R.L., Turin (IT)

(72) Inventors: Mauro Fiorini, Granarolo Dell'Emilia (IT); Paolo Fattori, Borgo Maggiore (SM)

(73) Assignee: STERIFY S.R.L., Turin (IT)

( * ) Notice: Subject to any disclaimer, the term of this patent is extended or adjusted under 35 U.S.C. 154(b) by 930 days.

(21) Appl. No.: 17/775,779

(22) PCT Filed: Nov. 19, 2020

(86) PCT No.: PCT/IB2020/060899
§ 371 (c)(1),
(2) Date: May 10, 2022

(87) PCT Pub. No.: WO2021/099981
PCT Pub. Date: May 27, 2021

(65) Prior Publication Data

US 2022/0387669 A1 Dec. 8, 2022

(30) Foreign Application Priority Data

Nov. 22, 2019 (IT) ........................ 102019000021876

(51) Int. Cl.

| | |
|---|---|
| ***A61L 27/52*** | (2006.01) |
| ***A61K 31/05*** | (2006.01) |
| ***A61L 27/26*** | (2006.01) |
| ***A61L 27/54*** | (2006.01) |

(52) U.S. Cl.
CPC .............. *A61L 27/52* (2013.01); *A61K 31/05* (2013.01); *A61L 27/26* (2013.01); *A61L 27/54* (2013.01); *A61L 2300/252* (2013.01); *A61L 2300/404* (2013.01); *A61L 2300/41* (2013.01)

(58) Field of Classification Search
CPC ...................................................... A61L 27/52
See application file for complete search history.

(56) References Cited

U.S. PATENT DOCUMENTS

| | | | | |
|---|---|---|---|---|
| 2007/0065943 | A1 | 3/2007 | Smith | |
| 2007/0275030 | A1* | 11/2007 | Muratoglu | C08J 3/075 424/487 |
| 2014/0180187 | A1 | 6/2014 | Croizat | |
| 2016/0032349 | A1 | 2/2016 | Farris | |
| 2017/0210843 | A1 | 7/2017 | Peeters et al. | |
| 2018/0135062 | A1 | 5/2018 | Wirth | |
| 2018/0296444 | A1 | 10/2018 | Jha | |

FOREIGN PATENT DOCUMENTS

| | | | |
|---|---|---|---|
| CN | 108815587 | A | 11/2018 |
| CN | 109588613 | A | 4/2019 |
| EA | 30364 | B1 | 7/2018 |
| EP | 3072401 | A1 | 9/2016 |
| RU | 2379025 | C2 | 1/2010 |
| RU | 2563232 | C1 | 9/2015 |
| RU | 2563238 | C1 | 9/2015 |
| RU | 2628539 | C2 | 8/2017 |
| WO | 2004052308 | A2 | 6/2004 |

OTHER PUBLICATIONS

Bermudez-Oria et al. Carbhydrate Polymers (2017) vol. 163 pp. 292-300.*

Fernandez-Bolanos et al. Current. Org. Chem. (2008) vol. 12(6) pp. 442-463.*

International Search Report and Written Opinion dated Feb. 22, 2021 from counterpart International Patent Application No. PCT/IB2020/060899.

European Office Action dated Mar. 5, 2024 from counterpart European App No. 20825234.6.

1st Russian Office Action dated Nov. 13, 2023 from counterpart Russian App No. 2022114312/04.

2nd Russian Office Action dated Mar. 6, 2024 from counterpart Russian App No. 2022114312/04.

3rd Russian Office Action dated Oct. 21, 2024 from counterpart Russian App No. 2022114312/04.

Hai Xiao et al., Acidic pH induces topoisomerase II-mediated DNA damage, PNAS, Apr. 29, 2003, vol. 100, No. 9, pp. 5205-5210.

T. Morita, et al., Clastogenicity of low pH to various cultured mammalian cells, Mutation Research, Aug. 1992; 268(2):297-305. doi: 10.1016/0027-5107(92)90235-t.

Takeshi Morita, Low pH leads to sister-chromatid exchanges and chromosomal aberrations, and its clastogenicity is S-dependent, Mutation Research 334 (1995), pp. 301-308.

H Lambers et al, Natural skin surface pH is on average below 5, which is beneficial for its resident flora, International Journal of Cosmetic Science, 2006, 28, pp. 359-370.

Hj Park, et al, Acidic environment causes apoptosis by increasing caspase activity, British Journal of Cancer (1999), 80(12), pp. 1892-1897.

Vishal Sharma et al, Low-pH-induced apoptosis: role of endoplasmic reticulum stress-induced calcium permeability and mitochondria-dependent signaling, Cell Stress and Chaperones, 2015, 20, pp. 431-440 DOI 10.1007/s12192-014-0568-6.

Zhu-Xu Zhang et al., Intracellular pH Regulates TRAIL-Induced Apoptosis and Necroptosis in Endothelial Cells, Journal of Immunology Research, vol. 2017, Article ID 1503960, pp. 1-10.

European Search report dated Nov. 18, 2025 from counterpart European App No. 20825234.6-1109.

Alejandra Bermudez-Oria et al: "Complexation of hydroxytyrosol and 3.4-dihydroxyphenylglycol with pectin and their potential use for colon targeting". Carbohydrate Polymers, vol. 163. May 1, 2017 (May 1, 2017). pp. 292-300.

Fernandez-Bolanos Jose G et al: "Hydroxytyrosol and Derivatives: Isolation. Synthesis. and Biological Properties". Current Organic Chemistry. Bentham Science Publishers. NL. vol. 12. No. 6. Apr. 1, 2008 (Apr. 1, 2008). pp. 442-463.

(Continued)

*Primary Examiner* — Paul V Ward
(74) *Attorney, Agent, or Firm* — SHUTTLEWORTH & INGERSOLL, PLC; Timothy J. Klima

(57) ABSTRACT

A controlled-viscosity polymeric hydrogel including an aqueous solvent, a water-soluble synthetic polymeric component and an anti-cross-linking component, constituted of a polyphenol, in particular of hydroxytyrosol.

17 Claims, No Drawings

(56) References Cited

OTHER PUBLICATIONS

Arthur Timothy D et al: "On bacteriocin delivery systems and potential applications". Future Microbiology. Future Medicine Ltd. GB. vol. 9. No. 2. Feb. 1, 2014 (Feb. 1, 2014). pp. 235-248.

European Office Action dated Jun. 26, 2024 from counterpart European App No. 20825235.3.

1st Russian Office Action dated Nov. 19, 2020 from counterpart Russian App No. 2022114312/04.

2nd Russian Office Action dated Feb. 13, 2024 from counterpart Russian App No. 2022114312/04.

G. Bisignano et al. On the In-vitro Antimicrobial Activity of Oleuropein and Hydroxytyrosol. Journal of Pharmacy and Pharmacology, vol. 51, Issue 8, Aug. 1999, pp. 971-974.

C. Piper et al. Bioengineering of a Nisin A-producing Lactococcus lactis to create isogenic strains producing the natural variants Nisin F, Q and Z. Microbial Biotechnology. 2010, vol. 4(3), pp. 375-382.

A. C. Molinos et al. Enhanced bactericidal activity of enterocin AS-48 in combination with essential oils, natural bioactive compounds and chemical preservatives against Listeria monocytogenes in ready-to-eat salad. Food and Chemical Toxicology. 2009, 47, pp. 2216-2223.

Kharkevich D. A. Farmakologiia/ Study book, 2010, 10th edition, pp. 76-77 Kharkevich D. A. Pharmacology/ Study book, 2010, 10th edition, pp. 76-77.

Lyamin A. V. et al. "Problemy v meditsine, sviazannye s bakter ialnymi plionkami. Klinicheskaia mikrobiologiia i antimikrobnaia khimioterapiia", 2012, vol. 14, No. 4, pp. 268-275 Lyamin A. V. et al. "Problems in Medicine Associated with Bacterial Biofilms. Clinical Microbiology and Antimicrobial Chemotherapy," 2012, vol. 14, No. 4, pp. 268-275(english).

Zhulenko V. N., Gorshkov G. I. Farmakologiia. ?.: KolosS, 2008, pp. 34-35) Zhulenko, V. N., & Gorshkov, G. I. *Pharmacology*. Moscow: Kolos, 2008, pp. 34-35.(english).

International Search Report and Written Opinion dated Mar. 12, 2021 from counterpart International Patent Application No. PCT/IB2020/060902.

Medina-Martinez Maria S. et al.: "Antimicrobial activity of hydroxytyrosol: a current controversy". Bioscience Biotechnology Biochemistry. Vol. 80. No. 4. Dec 18, 2015 (Dec. 18, 2015). pp. 801-810.

A study by M. Tre-Hardy et al. [53], when studying the effect of combining tobramycin with various macrolides, has shown an increase in effectiveness due to the synergism of the combination of tobramycin with clarithromycin. In contrast, the combination of tobramycin with azithromycin did not demonstrate synergism, and in some cases even led to antagonism (see p. 273, the right column).

3nd Russian Office Action dated Sep. 6, 2024 from counterpart Russian App No. 2022114312/04.

* cited by examiner

CONTROLLED-VISCOSITY POLYMERIC HYDROGEL AND METHOD FOR MAKING IT

This application is the National Phase of International Application PCT/IB2020/060899 filed Nov. 19, 2020 which designated the U.S.

This application claims priority to Italian Patent Application No. 102019000021876 filed Nov. 22, 2019, which application is incorporated by reference herein.

TECHNICAL FIELD

This invention relates to a controlled-viscosity polymeric hydrogel and the related method for making it.

In recent decades one of the sectors which has undergone the greatest development in the biomedical sphere is undoubtedly that of regenerative medicine: the discovery of the structure of DNA and the use of stem cells have allowed a considerable increase in situations in which there is a biological answer to biological problems.

One of the essential tools used by regenerative medicine is so-called tissue engineering, whose goal is to restore or improve the biological functions of damaged tissues and organs by recreating them, engineering them or promoting their repair.

In natural tissues the cells are immersed in an extracellular matrix (ECM) constituted of various types of biomolecules, mainly fibrous proteins, such as collagen and elastin, proteoglycans, and other polysaccharides, such as hyaluronic acid.

The dimensions of these biomolecules are between 50 and 500 nm and that has caused a natural interest in the use of nanomaterials and nanotechnologies in the tissue engineering sphere.

At present, three-dimensional frameworks, called "scaffolds" can be made in this way, which act as an extracellular matrix and organise the cells, directing their growth for the formation of the desired tissue.

In addition to supplying a supporting structure, the scaffold must fulfil other functions typical of the extracellular matrix, in particular cell proliferation, differentiation and migration, as well as having biomedical features consistent with the type of tissue to be regenerated. Finally, it will have to be biocompatible and biodegradable, so that it does not cause unwanted responses by the organism and so that it can be reabsorbed within a reasonable time without releasing products which are toxic for the organism itself.

BACKGROUND ART

Amongst the materials best suited to making scaffolds are polymers and hydrogels.

Natural polymers, such as collagen, glycosaminoglycans, chitin and chitosan, have been used in the repair of nerves, skin, cartilage and bone: although they are capable of simulating the natural cellular environment very well, the diversity and complexity of the stimuli they produce prevents full control of cellular development and differentiation.

Moreover, poor mechanical properties limited their use for the production of scaffolds.

In response to these problems many synthetic polymers have been made, such as polyglycolic acid (PGA), polylactic acid (PLA), polycaprolactone (PCL), polyvinylpyrrolidone (PVP), polyvinyl alcohol (PVA), or polymers of ethylene oxide, for example polyethylene glycol (PEG), also known as polyethylene oxide (PEO) or polyoxyethylene (POE).

Hydrogels are a class of hydrated polymeric materials with a high water content, present as up to 90% of the total weight.

Hydrogels are composed of a network of hydrophilic polymer chains interconnected by physical and chemical bonds.

The polymerization and cross-linkage process, also called "cross-linking", may be triggered physically, by regulating parameters, such as pressure, temperature, volume, in such a way as to start particular processes which result in the obtainment of a polymer network without adding chemical agents: one disadvantage of this method is the fact that inhomogeneities form inside the hydrogel which reduce its affinity to water.

For this reason, it is preferable to have a triggering of the polymerization and cross-linkage process, in which covalent bonds form between the polymer chains, preferably under the action of irradiation which quickly allows the obtainment of a hydrogel with chemical-physical, biological and mechanical properties which are optimised based on the specific use in the biomedical sphere.

The hydrogels used in scaffolds are biodegradable, have structural and mechanical properties similar to the extracellular matrix of many tissues and may be implanted in a minimally invasive way.

The materials usable for making hydrogels for scaffolds may be selected either amongst natural polymers (alginate, chitosan, collagen, fibrin, hyaluronic acid, etc.), or amongst synthetic polymers, such as polyacrylic acid (PAA), polyvinylpyrrolidone (PVP), polyvinyl alcohol (PVA), polyethylene glycol (PEG) and polypeptides.

In particular, synthetic polymers are widely used in the tissue engineering sphere, since their chemical properties are easily controllable and reproducible, allowing them the adaptability to replace a wide range of tissues.

In use, at least one of these biomaterials is selected for replacing the extracellular matrix of the connective tissues, for example a polymer of ethylene oxide (PEG, PEO or POE) and/or polyvinylpyrrolidone (PVP) and/or polyvinyl alcohol (PVA), it is rehydrated in aqueous solution and it is subjected to polymerization and sterilization by irradiation (for example, ß rays or γ rays): the main disadvantage of these materials is the fact that their degree of polymerization as a result of the irradiation is difficult to control and regulate, preventing forecasting of the viscosity and, consequently, the biomechanical behaviour with regard to the damaged tissue in which it is implanted.

To overcome this disadvantage, the making of hydrogels is known with additive components such as carotenoids, lipoic acid, vitamins such as vitamin E, vitamin B, vitamin D, ascorbic acid (vitamin C) or its derivatives, which are used as anti-cross-linking agents, which limit the irradiation-induced polymerization process thanks to their capacity for sequestering the free radicals which form as a result of the irradiation itself, as indicated in document US 2007/0275030 (Muratoglu et al.). In future, adding as additives components with a high antioxidant power seems to be the most effective method for controlling the viscosity of hydrogels obtained from synthetic polymers, at worst until what is obtained is a polymerized and sterilized hydrogel which has the same viscosity as before it was subjected to the irradiation.

DISCLOSURE OF THE INVENTION

The aim of this invention is therefore to eliminate the above-mentioned disadvantages.

The invention, with the features described in the claims, achieves the aim by using as an anti-cross-linking agent a polyphenol, in particular hydroxytyrosol.

The use of hydroxytyrosol in the formulation of polymeric hydrogels is indeed known, for example as illustrated in document US 2017/210843 (Peeters et al.), but it is used as a cross-linking agent in aqueous solutions with a pH greater than 6, which make it become unstable promoting its integration in the molecular chains which cause the polymerization of the hydrogel; therefore its action as an anti-cross-linking agent in aqueous solutions with a pH of less than 6 is surprising.

The main advantage obtained by means of this invention is essentially the fact that the very high antioxidant power of the hydroxytyrosol (or of another polyphenol) allows, depending on the doses used, precise control of the viscosity of the hydrogel: in particular, the hydroxytyrosol is capable of sequestering the polymer radical species which form as a result of the application of an electromagnetic radiation (for example, ß rays or γ rays or another source of ionizing radiation), in such a way as to limit the polymerization process and regulate the viscosity of the sterile final hydrogel.

Moreover, the fact that it is an amphipathic molecule (that is to say, with one lipophilic end and one hydrophilic end) gives hydroxytyrosol both the capacity to promote the hydration of polymers which are not very soluble in water, for example PEO, and to balance the hydration of mixtures of polymers with very different solubilities, such as, for example, those constituted of PVA (highly soluble) and PEO (not very soluble).

Moreover, to the hydrogel obtained in this way, it is possible to add as additives collagen peptides and/or bacteriocins for strengthening its regenerative and anti-inflammatory properties, as well as for enhancing its antimicrobial properties.

Further advantages and features of the invention will be more apparent in the detailed description below.

PREFERRED EMBODIMENTS OF THE INVENTION

A controlled-viscosity polymeric hydrogel comprises an aqueous solvent with a pH of less than 6, a water-soluble synthetic polymeric component and an anti-cross-linking component, wherein the anti-cross-linking component is constituted of a polyphenol, preferably of hydroxytyrosol or another polyphenolic derivative, such as, for example, oleuropein and tyrosol, but also oleocanthal and/or oleacein.

In the method for making the controlled-viscosity hydrogel, after having rehydrated the synthetic polymeric component in aqueous solution having a pH of less than 6, the solution has added to it as an additive hydroxytyrosol (or its derivative), or another polyphenol.

Hydroxytyrosol is a plant chemical compound present in olive oil: it and its derivatives are used here because of the very high antioxidant power, that is to say, because of the capacity to capture the free radicals which form as a result of some electrochemical reactions. In this case, when the solution is irradiated with an electromagnetic radiation preferably having a frequency within the frequency spectrum of ß rays or of γ rays, the hydroxytyrosol limits the polymerization process, capturing the polymer radical species in such a way as to control the final viscosity of the sterilized hydrogel.

Based on the final viscosity, the hydrogel obtained may be used in the tissue regeneration sphere and in the treatment of connective tissue infections: the presence of the hydroxytyrosol accounts for the anti-inflammatory and regenerative properties which the hydrogel may have once implanted, in particular in epithelial, connective, muscular and nerve tissues.

Strengthening of the regenerative and anti-inflammatory power of the hydrogel may be achieved thanks to the addition of collagen peptides, for example of bovine origin, which are capable of stimulating new collagen synthesis, in particular for bone, cartilage, tendons, ligaments and skin; the increase in the antimicrobial potential may in contrast be achieved with the addition as additives of bacteriocins, in particular of class I, which are particularly effective against antibiotic-resistant pathogens.

The water-soluble synthetic polymeric component is selected from a group comprising a polymer and/or polymeric mixtures and/or copolymers of ethylene oxide (PEG, PEO, POE), vinyl alcohol, vinyl pyrrolidone, its average molecular weight is between 300 and 10,000,000 g/mol, and preferably between 1,000 and 3,000,000 g/mol, and its quantity by weight is between 1% and 30% of the total weight of the hydrogel.

The concentration of hydroxytyrosol is equal to or less than 100 mM, and preferably equal to or less than 50 mM.

The collagen peptides have a molecular weight equal to or less than 5,000 g/mol, and preferably equal to or less than 3,000 g/mol, their concentration is equal to or less than 50 mg/ml, and preferably equal to or less than 25 mg/ml.

The class I bacteriocins, which include Nisin A, Nisin F and/or Nisin Z, have a concentration equal to or less than 10 mM, and preferably equal to or less than 5 mM.

The invention claimed is:

1. A controlled-viscosity polymeric hydrogel, comprising an aqueous solvent, a water-soluble synthetic polymeric component and an anti-cross-linking component, wherein the aqueous solvent has a pH ranging between 4 and 6 and that the anti-cross-linking component is hydroxytyrosol, oleuropein, tyrosol, oleocanthal and/or oleacein.

2. The hydrogel according to claim 1, wherein the water-soluble synthetic polymeric component has an average molecular weight of between 300 and 10,000,000 g/mol.

3. The hydrogel according to claim 1, wherein the water-soluble synthetic polymeric component has an average molecular weight of between 1,000 and 3,000,000 g/mol.

4. The hydrogel according to claim 1, wherein a concentration of the hydroxytyrosol, oleuropein, tyrosol, oleocanthal and/or oleacein is equal to or less than 100 mM.

5. The hydrogel according to claim 1, wherein a concentration of the hydroxytyrosol, oleuropein, tyrosol, oleocanthal and/or oleacein is equal to or less than 50 mM.

6. The hydrogel according to claim 1, wherein a quantity by weight of the water-soluble synthetic polymeric component is between 1% and 30% of a total weight of the hydrogel.

7. The hydrogel according to claim 1, and further comprising collagen peptides to increase a regenerative and anti-inflammatory capacity.

8. The hydrogel according to claim 1, and further comprising bacteriocins to increase an antimicrobial capacity.

9. The hydrogel according to claim 7, wherein the collagen peptides have a molecular weight equal to or less than 5,000 g/mol.

10. The hydrogel according to claim 7, wherein the collagen peptides have a molecular weight equal to or less than 3,000 g/mol.

11. The hydrogel according to claim 7, wherein a concentration of the collagen peptides is equal to or less than 50 mg/ml.

12. The hydrogel according to claim 7, wherein a concentration of the collagen peptides is equal to or less than 25 mg/ml.

13. The hydrogel according to claim 8, and further comprising class I bacteriocins, selected from a group consisting of Nisin A, Nisin F and/or Nisin Z.

14. The hydrogel according to claim 8, wherein a concentration of the bacteriocins is equal to or less than 10 mM.

15. The hydrogel according to claim 8, wherein a concentration of the bacteriocins is equal to or less than 5 mM.

16. The hydrogel according to claim 1, wherein the water-soluble synthetic polymeric component is selected from a group comprising a polymer and/or polymeric mixtures and/or copolymers of PEG, PEO, POE, vinyl alcohol, vinyl pyrrolidone.

17. A method for making a controlled-viscosity polymeric hydrogel, comprising the following steps:

rehydration of a synthetic polymeric component in aqueous solution with a pH ranging between 4 and 6;

addition of a polyphenol additive to the solution, wherein the additive is selected from hydroxytyrosol, oleuropein, tyrosol, oleocanthal and/or oleacein;

irradiation of the solution with an electromagnetic radiation having a frequency within a frequency spectrum of ß rays or of γ rays;

polymerization of the hydrogel, limited by an antioxidant property of the additive.

* * * * *